(12) United States Patent
Connolly et al.

(10) Patent No.: US 11,766,586 B2
(45) Date of Patent: Sep. 26, 2023

(54) ORTHOSTATIC HYPOTENSION ALLEVIATION DEVICE

(71) Applicant: Medicon Ireland Limited, Newry (GB)

(72) Inventors: Lochlainn Connolly, Belfast (GB); Neil Fawkes, Belfast (GB); Ignatius McGowan, Belfast (GB)

(73) Assignee: Medicon Ireland Limited, Newry (GB)

( * ) Notice: Subject to any disclaimer, the term of this patent is extended or adjusted under 35 U.S.C. 154(b) by 0 days.

(21) Appl. No.: 17/792,828

(22) PCT Filed: Jan. 27, 2021

(86) PCT No.: PCT/GB2021/050191
§ 371 (c)(1),
(2) Date: Jul. 14, 2022

(87) PCT Pub. No.: WO2021/152308
PCT Pub. Date: Aug. 5, 2021

(65) Prior Publication Data
US 2023/0044812 A1 Feb. 9, 2023

(30) Foreign Application Priority Data
Jan. 31, 2020 (GB) ..................................... 2001385

(51) Int. Cl.
*A63B 21/00* (2006.01)
*A63B 21/002* (2006.01)
(Continued)

(52) U.S. Cl.
CPC .......... *A63B 21/153* (2013.01); *A63B 21/002* (2013.01); *A63B 21/00185* (2013.01);
(Continued)

(58) Field of Classification Search
CPC ............ A63B 21/153; A63B 21/00185; A63B 21/002; A63B 21/025; A63B 21/0421;
(Continued)

(56) References Cited

U.S. PATENT DOCUMENTS 3,576,233 A * 4/1971 Thatcher ................... E04G 1/20
182/69.6
4,135,714 A * 1/1979 Hughes .................. A63B 21/04
473/229
(Continued)

FOREIGN PATENT DOCUMENTS

GB          2526093 A     11/2015
WO      2018101524 A1      6/2018

OTHER PUBLICATIONS

International Search Report for PCT Application No. PCT/GB2021/050191; dated Apr. 20, 2021; three (3) pages.
(Continued)

*Primary Examiner* — Garrett K Atkinson
(74) *Attorney, Agent, or Firm* — Gerald Hespos; Michael Porco (57) ABSTRACT

An orthostatic hypotension alleviation device comprising an outer casing comprising an aperture extending therethrough; a carriage arranged within the outer casing and configured to be reciprocally displaced towards and away from the aperture along a carriage displacement axis; a spindle arranged on the carriage and configured to rotate about a spindle axis; a tether at least partially wound around the spindle, the tether comprising a distal end extending through the aperture, the tether being arranged such that it can be extended from a retracted configuration to an extended configuration in which the tether is fully extended by pulling the distal end away from the aperture so rotating the spindle about the spindle axis; a spindle biasing mechanism connected to the spindle and configured to apply a biasing torque to the
(Continued)

spindle about the spindle axis so as to bias the tether towards the retracted configuration; and, a carriage biasing mechanism arranged within the outer casing connected to the carriage and configured to bias the carriage away from the aperture.

14 Claims, 8 Drawing Sheets

(51) Int. Cl.
*A63B 21/02* (2006.01)
*A63B 21/04* (2006.01)

(52) U.S. Cl.
CPC ........ *A63B 21/025* (2013.01); *A63B 21/0421* (2013.01); *A63B 21/4021* (2015.10); *A63B 2220/13* (2013.01); *A63B 2220/40* (2013.01); *A63B 2220/833* (2013.01); *A63B 2230/04* (2013.01)

(58) Field of Classification Search
CPC ............ A63B 21/4021; A63B 2220/13; A63B 2220/40; A63B 2220/833; A63B 2230/04; A63B 21/0004; A63B 21/4043; A63B 71/0054; A63B 2022/0097; A63B 2230/06; A63B 2230/30; A63B 21/022; A63B 21/023; A63B 21/154; A61B 5/6895; A61B 5/021
See application file for complete search history.

(56) References Cited

U.S. PATENT DOCUMENTS

| | | | | | |
|---|---|---|---|---|---|
| 4,328,965 | A | * | 5/1982 | Hatfield | F41B 5/1476 482/122 |
| 4,685,670 | A | * | 8/1987 | Zinkin | A63B 21/169 482/904 |
| 4,779,866 | A | * | 10/1988 | Marshall | A63B 21/00069 482/116 |
| 4,961,573 | A | * | 10/1990 | Wehrell | A63B 21/4007 482/124 |
| 4,979,733 | A | * | 12/1990 | Prud'Hon | A63B 21/0058 482/901 |
| 5,090,694 | A | * | 2/1992 | Pauls | A63B 21/015 482/904 |
| 5,147,265 | A | * | 9/1992 | Pauls | A63B 23/12 482/115 |
| 5,226,867 | A | * | 7/1993 | Beal | A63B 21/025 482/127 |
| 5,382,212 | A | * | 1/1995 | Davenport | A63B 21/04 482/121 |
| 5,486,149 | A | * | 1/1996 | Smith | A63B 21/4043 482/904 |
| 5,586,962 | A | * | 12/1996 | Hallmark | A63B 21/4007 482/129 |
| 5,618,249 | A | * | 4/1997 | Marshall | A63B 21/4001 482/92 |
| 5,697,869 | A | | 12/1997 | Ehrenfried et al. | |
| 5,733,231 | A | * | 3/1998 | Corn | A63B 21/153 482/127 |
| 6,099,447 | A | | 8/2000 | Ramsaroop | |
| 6,120,423 | A | | 9/2000 | Mackey et al. | |
| 6,436,006 | B1 | * | 8/2002 | Zemlyakov | A63B 21/00069 482/112 |
| 6,440,044 | B1 | * | 8/2002 | Francis | A63B 21/4043 482/137 |
| 6,685,602 | B2 | * | 2/2004 | Colosky, Jr. | A63B 21/025 482/904 |
| 6,929,589 | B1 | * | 8/2005 | Bruggemann | A63B 21/025 482/904 |
| 7,087,001 | B1 | | 8/2006 | Ihli | |
| 7,137,936 | B1 | * | 11/2006 | Shaw | A63B 21/153 482/79 |
| 7,462,141 | B1 | * | 12/2008 | Raboin | A63B 21/225 482/110 |
| 7,871,359 | B2 | * | 1/2011 | Humble | A63B 21/025 482/121 |
| 7,878,955 | B1 | * | 2/2011 | Ehrlich | A63B 21/025 482/127 |
| 8,002,677 | B2 | * | 8/2011 | Dibble | A63B 21/4047 482/92 |
| 9,320,936 | B1 | * | 4/2016 | Rea | A63B 23/1209 |
| 9,802,095 | B1 | | 10/2017 | Boyer et al. | |
| 10,046,195 | B2 | * | 8/2018 | Scheffer | A63B 21/1618 |
| 2002/0025891 | A1 | * | 2/2002 | Colosky, Jr. | A63B 21/0455 482/127 |
| 2005/0181915 | A1 | * | 8/2005 | Hoecht | A63B 21/023 482/121 |
| 2010/0016132 | A1 | | 1/2010 | Flynn | |
| 2010/0130338 | A1 | * | 5/2010 | Wehrell | A63B 21/4007 473/215 |
| 2010/0317488 | A1 | | 12/2010 | Cartaya | |
| 2014/0357457 | A1 | | 12/2014 | Boekema | |
| 2015/0374290 | A1 | | 12/2015 | Spears et al. | |
| 2016/0206912 | A1 | * | 7/2016 | Carriere, Jr. | A63B 21/0428 |
| 2018/0368738 | A1 | | 12/2018 | Tong et al. | |
| 2019/0344123 | A1 | | 11/2019 | Rubin et al. | |
| 2023/0009699 | A1 | * | 1/2023 | Ferlito | A63B 21/0552 |

OTHER PUBLICATIONS

Nagaya Sachiko et al: "The Effect of Ankle Exercise on Cerebral Blood Oxygenation During and After Postural Change", May 30, 2018 (May 30, 2018), Advances in Databases and Information Systems; [Lecture Notes in Computer Science; Lect.Notes Computer], Springer International Publishing, Cham, pp. 183-192, XP047498199, ISBN: 978-3-319-10403-4.
UK Combined Search and Examination Report for Application No. GB2001385.0; dated Jul. 16, 2020; eight (8) pages.
UK Search Report for Application No. GB2101099.6; dated Jul. 14, 2021; three (3) pages.

* cited by examiner

ORTHOSTATIC HYPOTENSION ALLEVIATION DEVICE

This application is a U.S. national phase application of PCT Application no. PCT/GB2021/050191 filed on Jan. 27, 2021, which claims priority to United Kingdom Patent Application No. GB 2001385.0 filed on Jan. 31, 2020, the disclosure of which is hereby incorporated by reference.

The present invention relates to an orthostatic hypotension alleviation device. More particularly, but not exclusively, the present invention relates to an orthostatic hypotension alleviation device comprising a carriage arranged in an outer casing and having a spindle thereon with a tether at least partially wrapped around the spindle, the carriage being biased away from the outer casing by a carriage biasing mechanism and the tether being biased in a retracted configuration by means of a spindle biasing mechanism connected to the spindle.

In a healthy state the human body can rapidly detect and correct changes in blood pressure caused by changing from a resting position (sitting or lying down) to an upright position. Orthostatic Hypotension (OH) is a condition that represents a failure of the bodies reflex systems (autonomic nervous system), resulting in a patient's blood pressure failing to adjust upon postural changes or from extended periods of quiet standing. This deficit in blood pressure causes reduced blood flow to the anatomically superior parts of the body, such as the head. This can cause light-headedness, dizziness, faintness, visual change, weakness, cognitive impairment, syncope, angina and stroke. The secondary sequelae are of greater concern, such as falls resulting in hospitalisation which can be commonly associated with debilitating prognosis, such as brain injury, fractures, immobility, etc. OH may sound physiologically benign on paper, but it can have far reaching impact to patients owing to its prevalence and prognosis.

Current treatments for OH include non-pharmacological treatments, such as avoiding causative medications, increasing hydration, drinking water bolus before standing, dietary restrictions and physical compression garments or physical compression manoeuvres. However, these treatments are generally not practical, can be complex or uncomfortable or are rendered ineffective due to poor patient compliance.

The types of physical compression manoeuvres are restricted clinically and often difficult to perform unaided in the patient population who suffer from OH. Performing an isokinetic exercise (e.g. such as lifting a weight prior to standing) may cause a rise in the patient's blood pressure. However, this is not recommended due to an uncorrelated relationship between blood pressure and the speed and force with which the patient performs the exercise. This can lead to large swings in blood pressure potentially exceeding the safe therapeutic window which could lead to complications such as stroke, or rupture of aneurysm.

The present invention seeks to overcome the problems of the prior art.

Accordingly, the present invention provides an orthostatic hypotension alleviation device comprising an outer casing comprising an aperture extending therethrough;

a carriage arranged within the outer casing and configured to be reciprocally displaced towards and away from the aperture along a carriage displacement axis;

a spindle arranged on the carriage and configured to rotate about a spindle axis;

a tether at least partially wound around the spindle, the tether comprising a distal end extending through the aperture, the tether being arranged such that it can be extended from a retracted configuration to an extended configuration in which the tether is fully extended by pulling the distal end away from the aperture so rotating the spindle about the spindle axis;

a spindle biasing mechanism connected to the spindle and configured to apply a biasing torque to the spindle about the spindle axis so as to bias the tether towards the retracted configuration; and, a carriage biasing mechanism arranged within the outer casing connected to the carriage and configured to bias the carriage away from the aperture.

The device according to the invention employs two biasing mechanisms. This enables a patient to extend the tether with little force so reducing the undesirable effects of performing an isokinetic exercise but then perform an isometric exercise against the relatively strong biasing force provided by the carriage biasing mechanism once the tether is extended.

Preferably the carriage biasing mechanism is connected between the carriage and outer casing.

Preferably the carriage biasing mechanism comprises at least one carriage biasing spring extending along an axis substantially parallel to the carriage displacement axis.

Preferably the carriage biasing spring has a spring constant k, k having a value such that as the pulling force on the tether is increased to a value at which the spindle first begins to turn then at that value the carriage biasing spring is partially compressed or partially extended.

Preferably the carriage biasing spring has a spring constant k, the value of k being such that when a pulling force $P_c$ is applied to the tether which produces a torque on the spindle which balances the torque applied to the spindle by the spindle biasing mechanism, the carriage biasing spring is partially compressed or partially extended.

Preferably the spindle biasing mechanism is connected between the spindle and carriage.

Preferably the spindle biasing mechanism comprises a clockwork spring.

Preferably the carriage comprises a carriage plate and an inner casing connected to the carriage plate, the spindle and spindle biasing mechanism being arranged within the inner casing.

Preferably the inner casing is detachably connected to the carriage plate.

Preferably the orthostatic hypotension alleviation device further comprises a position detection mechanism for detecting the position of the carriage along the carriage displacement axis.

Preferably the position detection mechanism comprises first and second electrical contacts arranged inside the outer casing with the first contact proximate to the second, the first and second contact being arranged such that as the carriage moves along the displacement axis it abuts the first contact urging it into contact with the second contact.

Preferably the orthostatic hypotension alleviation device further comprises at least one of an accelerometer, a blood pressure sensor and a pulse monitor.

Preferably the orthostatic hypotension alleviation device further comprises a strap connected to the outer casing for connection to the human body.

Preferably, the strap is a wrist strap.

The present invention will now be described by way of example only and not in any limitative sense with reference to the accompanying drawings in which.

Figure 1:
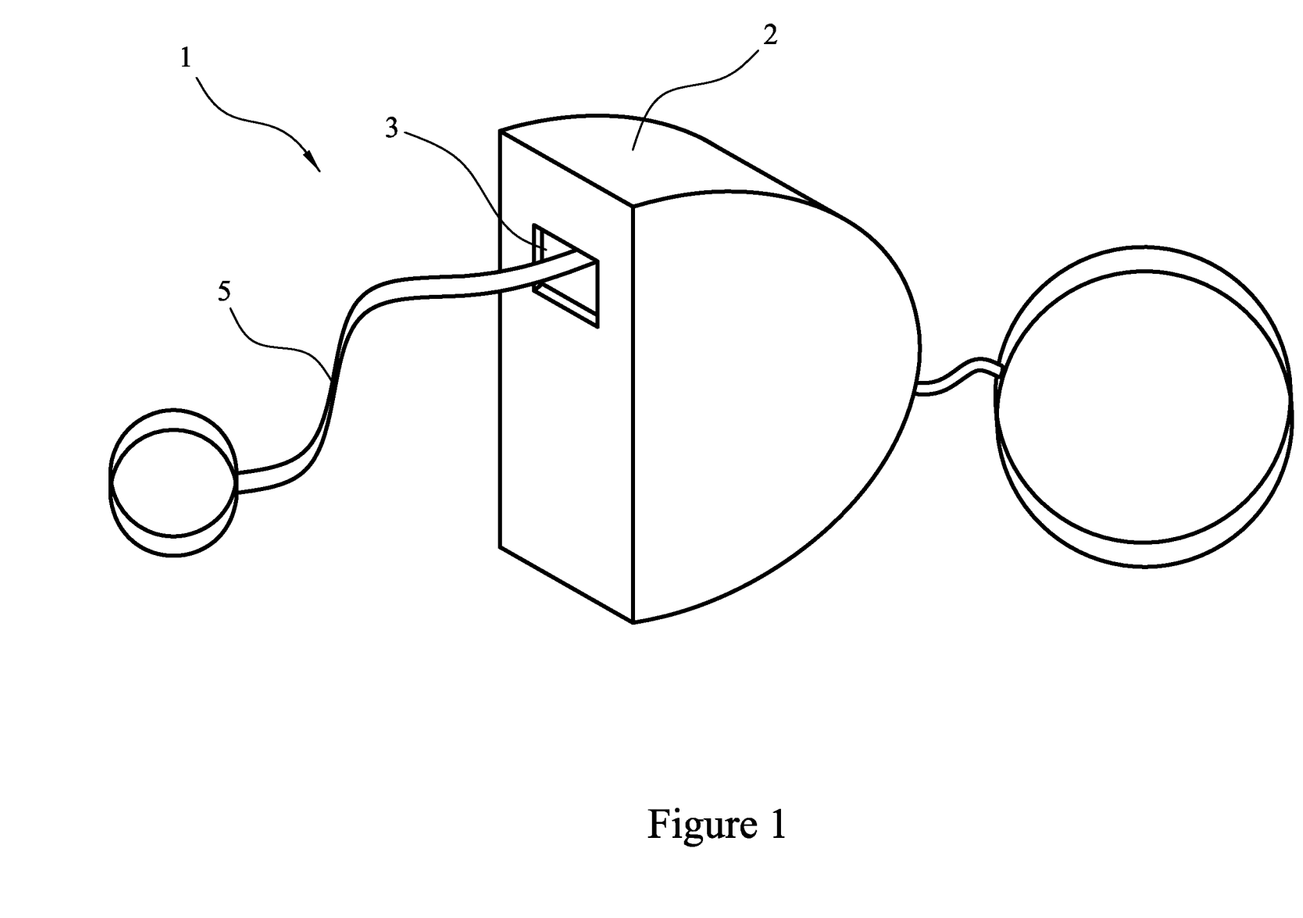
FIG. 1 shows a known device for use in the exercise field.

Shown in FIG. 1 is a known exercise device 1. The device 1 comprises a casing 2 which has an aperture 3 extending therethrough. Attached to the outside of the casing 2 is a loop 4. Arranged within the casing 2 is a spindle (not shown) which is free to rotate about a spindle axis. Wrapped around the spindle and extending through the aperture 3 is a tether 5.

In use a user attaches the loop 4 to one of their feet. The user then grips the tether 5 and pulls it upwards and out of the casing 2, extending the tether 5 from a retracted configuration to an extended configuration, so performing an isokinetic exercise. An adjustable biasing means within the casing 2 biases the tether 5 towards the retracted configuration so controlling the work done by the user when extending the tether 5.

Whilst such a device 1 finds application in the field of personal exercise it is unsuitable for use as a orthostatic hypotension alleviation device. In fact, use of such a device by a patient to alleviate orthostatic hypotension may be dangerous. The exercise performed by a user is an isokinetic exercise (i.e. one which involves contraction of muscle against a resistance at a substantially fixed speed). There is an uncorrelated relationship between blood pressure and the speed and force with which the user performs the exercise. This can lead to large swings in blood pressure potentially exceeding the safe therapeutic window which could lead to complications such as stroke, or rupture of aneurysm.

Figure 2:
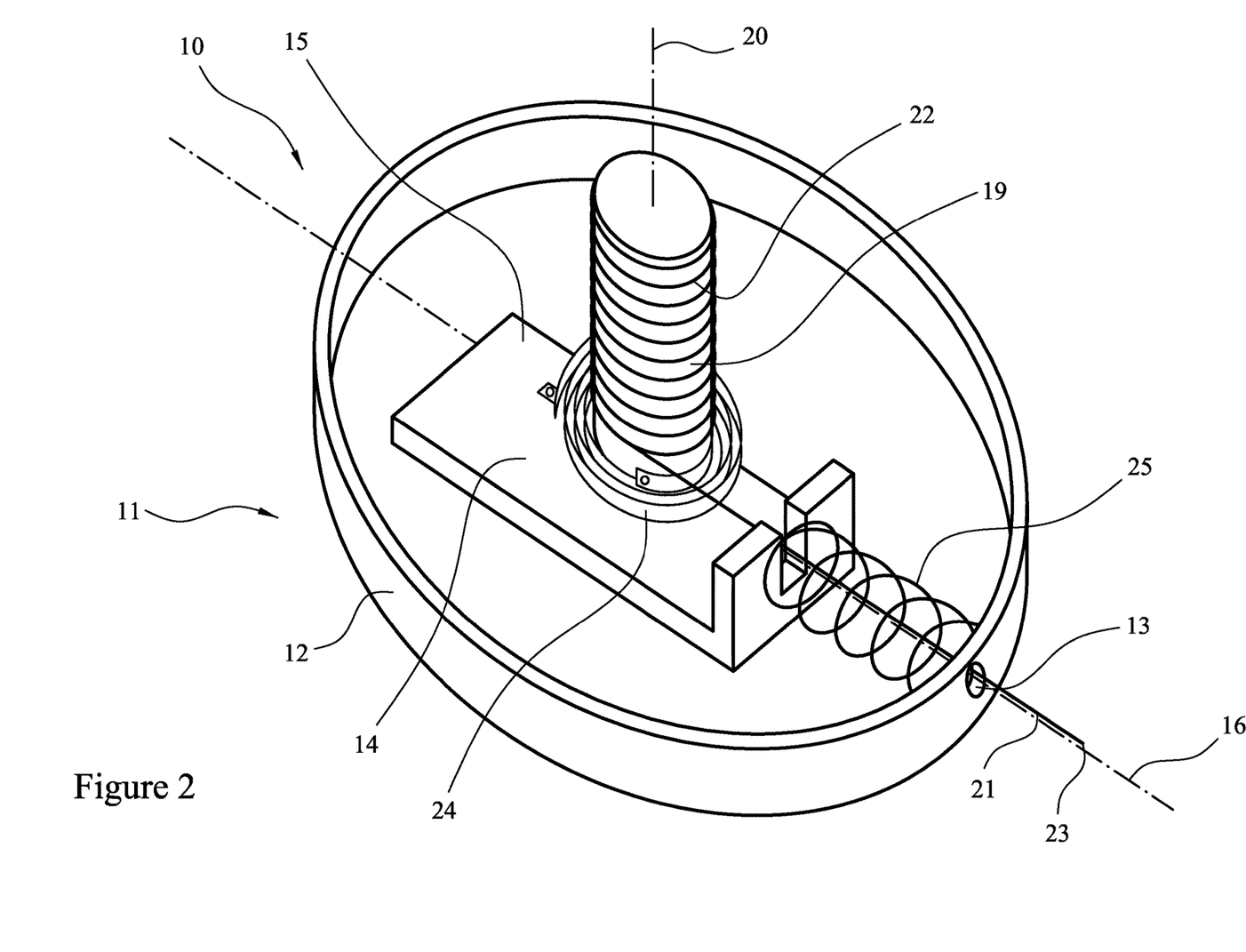
FIG. 2 shows a first embodiment of a device according to the invention.

Shown in FIG. 2 in schematic form is a first embodiment of an orthostatic hypotension alleviation device 10 according to the invention. The device 10 comprises an outer casing 11 defined by an outer casing wall 12. Extending through the outer casing wall 12 is an aperture 13. The top half of the outer casing 11 is not shown so that the contents of the outer casing 11 can be seen.

Arranged within the outer casing 11 is a carriage 14 comprising a carriage plate 15. The carriage plate 15 is configured to be reciprocally displaced towards and away from the aperture 13 along a carriage displacement axis 16.

Figure 3:
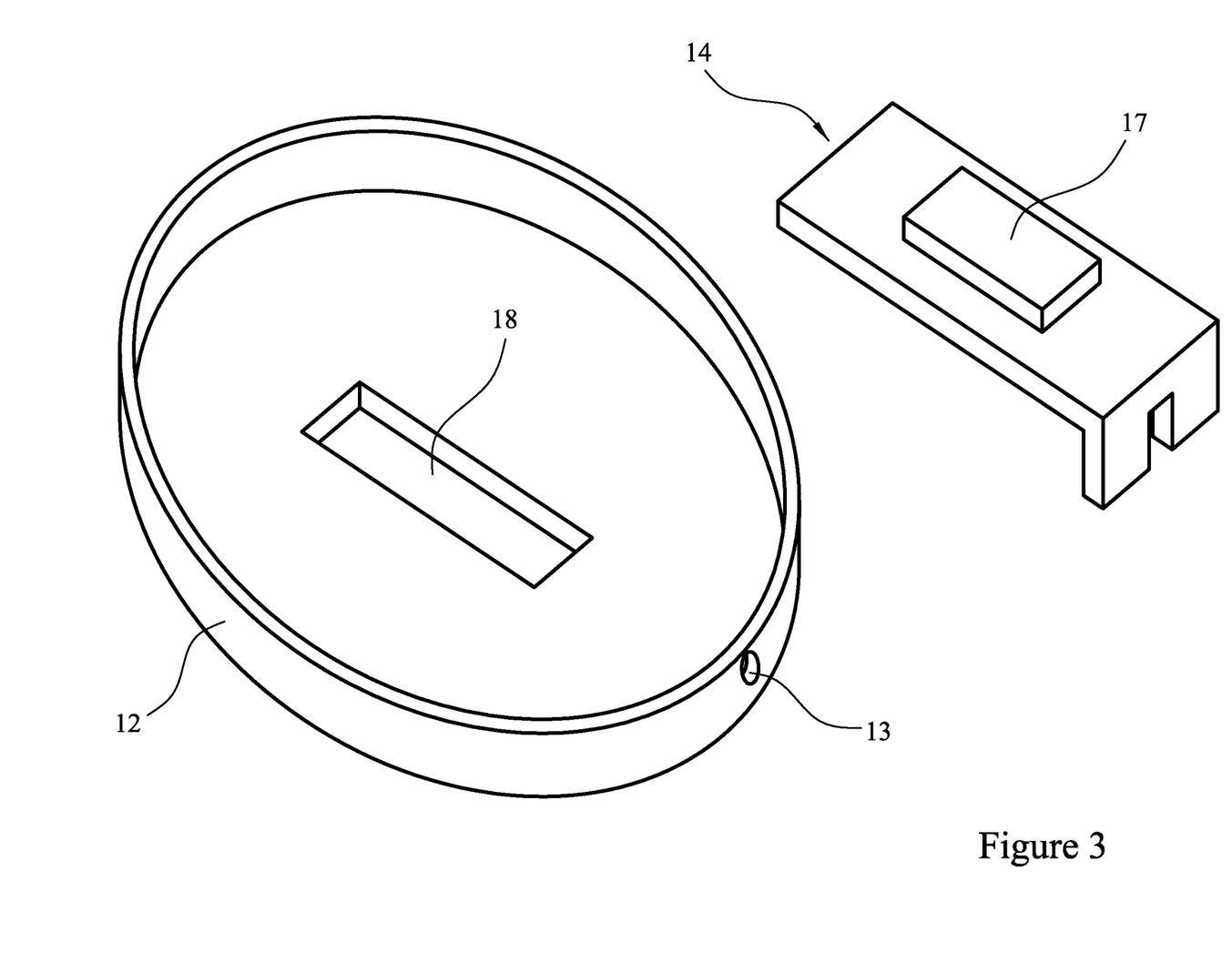
FIG. 3 shows the underside of the carriage of the device of FIG. 2.

FIG. 3 shows the underside of the carriage 14 and a portion of the outer casing wall 12. The underside of the carriage 14 comprises a tongue 17. Arranged in the outer casing wall 12 is a corresponding groove 18. In use the tongue 17 is arranged in the groove 18 so constraining the carriage 14 to move along the carriage displacement axis 16.

Returning to FIG. 2, the device 10 further comprises a spindle 19 arranged on the carriage plate 15. The spindle 19 is free to rotate about a spindle axis 20 which in this embodiment is substantially normal to the carriage displacement axis 16.

Partially wrapped around the spindle 19 is a tether 21. A proximate end 22 of the tether 21 is connected to the spindle 19. A distal end 23 of the tether 21 extends through the aperture 13 in the outer casing wall 12 as shown. In FIG. 2 the tether 21 is shown in a retracted configuration with the majority of the tether 21 wrapped around the spindle 19 with only the distal end 23 of the tether 21 extending through the aperture 13 in the outer casing 11. By pulling on the distal end 23 of the tether 21 away from the aperture 13 the spindle 19 rotates so extending the tether 21 to an extended configuration. In the extended configuration the tether 21 is no longer wrapped around the spindle 19 and so pulling the tether 21 further does not cause any further rotation of the spindle 19. This is explained in more detail below.

Connected between the spindle 19 and the carriage 14 is a spindle biasing mechanism 24. In this embodiment the spindle biasing mechanism 24 is a clockwork spring 24. For clarity only the two ends of the clockwork spring 24 are shown. The spindle biasing mechanism 24 is configured to apply a torque to the spindle 19 about the spindle axis 20 so as to bias the tether 21 towards the retracted configuration. If one were to partially extend the tether 21 and then release it the torque applied by the spindle biasing mechanism 24 on the spindle 19 would cause the spindle 19 to rotate, so retracting the tether 21 until it reaches the retracted configuration.

The device 10 further comprises a carriage biasing mechanism 25 arranged between the carriage 14 and outer casing 11. The carriage biasing mechanism 25 is configured to bias the carriage 14 away from the aperture 13. In this embodiment the carriage biasing mechanism 25 comprises a carriage biasing spring 25 having a spring constant K, and which extends along an axis substantially parallel to the carriage displacement axis 16.

Figure 4A:
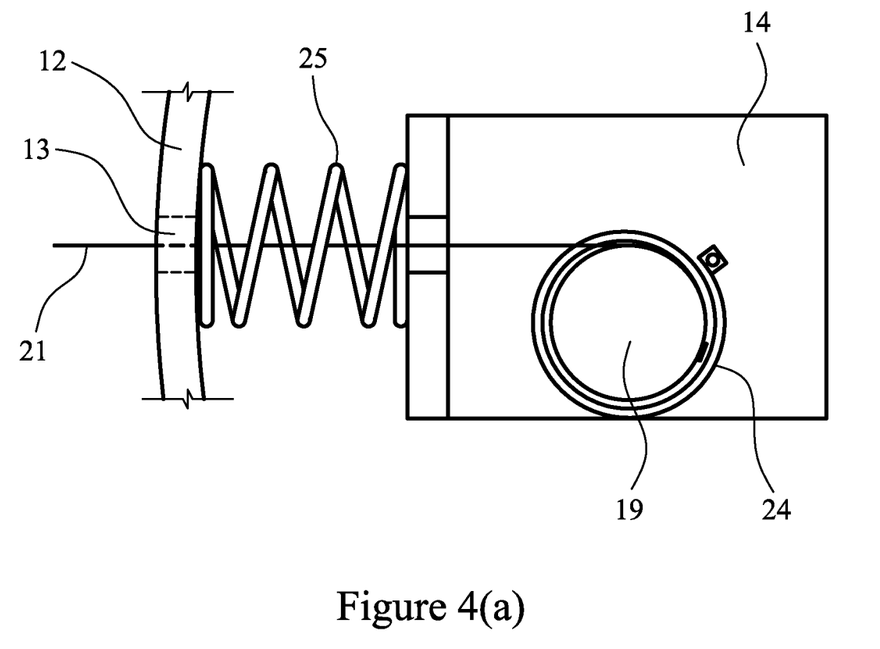
FIGS. 4(a) to 4(d) show the operation of the device of FIG. 2.
Figure 4B:
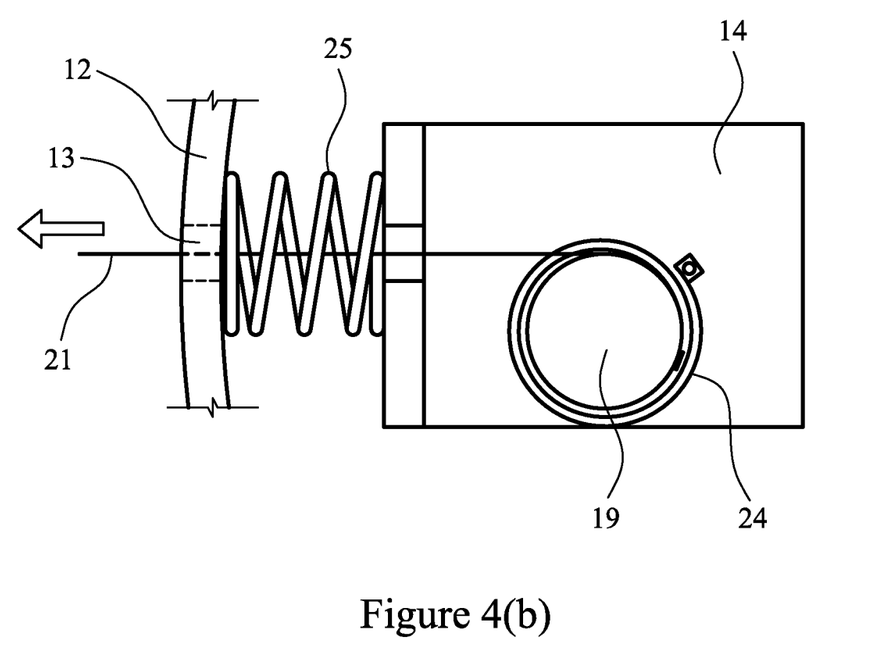

FIG. 4(a) shows the device 10 from above in schematic form with the tether 21 in the retracted configuration. Again, for clarity only the end of the clockwork spring 24 is shown. Also, only a portion of the outer casing wall 12 proximate to the aperture 13 is shown. In use the patient grips the outer casing 11 in one hand and the distal end of the tether 21 in the other. Alternatively, as the device 10 is relatively compact it can be connected to the wrist by means of a wrist strap connected to the outer casing 11, so allowing one handed operation. The patient then starts to pull the distal end 23 of the tether 21. Initially the force applied by the patient is small. This pulling force produces a tension in the tether 21 which in turn produces a torque on the spindle 19 about the spindle axis 20. This torque is less than the torque applied by the clockwork spring 24 on the spindle 19 about the spindle axis 20 in the opposite direction and so the spindle 19 does not rotate. The tension however causes a small degree of compression of the carriage biasing spring 25 so displacing the carriage 14 slightly along the carriage displacement axis 16 towards the aperture 13 as shown in FIG. 4(b).

The patient then increases the pulling force on the tether 21 to a value $P_c$. At this point the torque exerted on the spindle 19 about the spindle axis 20 balances the torque applied to the spindle 19 by the spindle biasing mechanism 24 in the opposite direction.

Figure 4C:
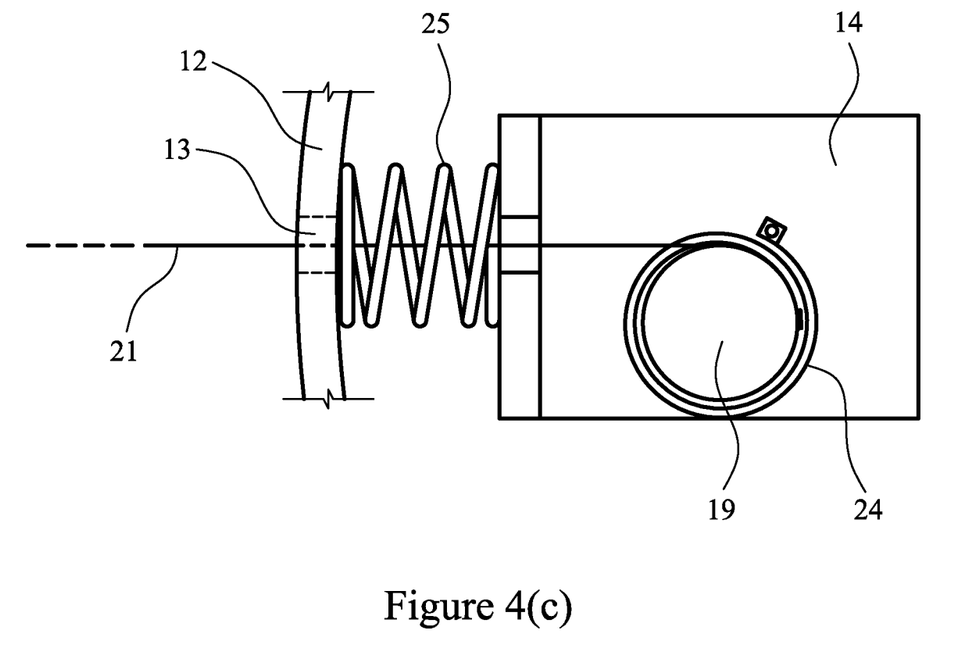

The patient then increases the pulling force on the tether 21 to exceed $P_c$. The torque produced by the tether 21 on the spindle 19 then exceeds the torque in the opposite direction produced by the clockwork spring 24. The spindle 19 therefore starts to rotate and by maintaining this pulling force the patient can extend the tether 21 from the retracted configuration to the extended configuration as shown in FIG. 4(c). In the extended configuration the tether 21 is completely unwound from the spindle 19 and so the spindle 19 will not rotate any further.

The torque applied to the spindle 19 by the clockwork spring 24 is relatively small. Accordingly, the tether 21 can be pulled from the outer casing 11 from the retracted configuration to the extended configuration without difficulty by the patient. Whilst the patient is performing an isokinetic exercise at this point, the forces involved are small and do not cause any significant increase in the blood pressure of the patient.

Figure 4D:
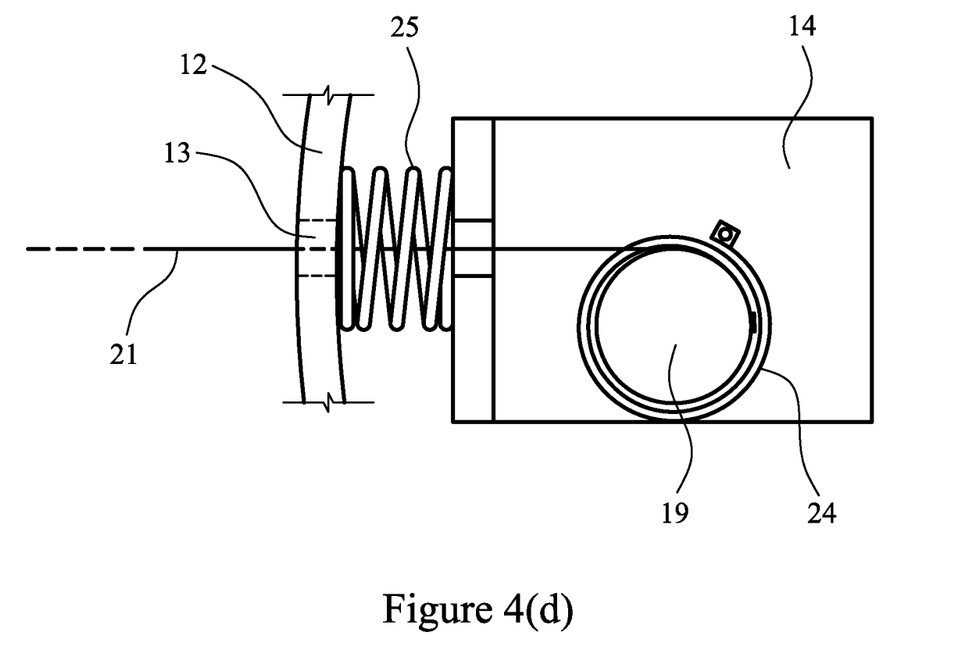

Once the tether 21 is in the extended configuration, the patient then increases the pulling force further. As the spindle 19 no longer rotates, this increase in pulling force causes the carriage biasing spring 25 to compress as shown in FIG. 4(d). The carriage biasing spring 25 is a relatively stiff spring (i.e. has a high spring constant) and so a relatively large increase in pulling force is required to produce any substantive compression of the carriage biasing spring 25.

Once the patient is pulling the tether 21 with the desired pulling force (which is typically in the range of 20-100 N) the patient then holds the tether 21 stationary against the biasing force of the carriage biasing spring 25, so performing an isometric exercise (i.e. one where a force is exerted but the is no lengthening or shortening of muscle). The isometric exercise produces a controlled increase in the blood pressure of the patient. Once the tether 21 has been held by the patient against the biasing force of the carriage biasing spring 25 for the desired period of time, the patient then releases the tether 21 which is retracted back to the retracted configuration by the clockwork spring 24.

Generally speaking, the carriage biasing spring 25 has a spring constant k. The value of k is such that when a pulling force $P_c$ is applied to the tether 21 so as to produce a torque at the spindle 19 which balances the torque applied to the spindle 19 by the spindle biasing mechanism 24, the carriage biasing spring 25 is partially compressed. To put this another way, as the pulling force on the tether 21 is increased to a value at which the spindle 19 first begins to turn, then at this value of pulling force the carriage biasing spring 25 is partially compressed. If the spring constant were too small the carriage biasing spring 25 would fully compress before the spindle 19 started to turn. The patient would then not be able to perform a subsequent controlled isometric exercise by compressing the carriage biasing spring 25 further after the tether 21 had reached the extended configuration.

Figure 5:
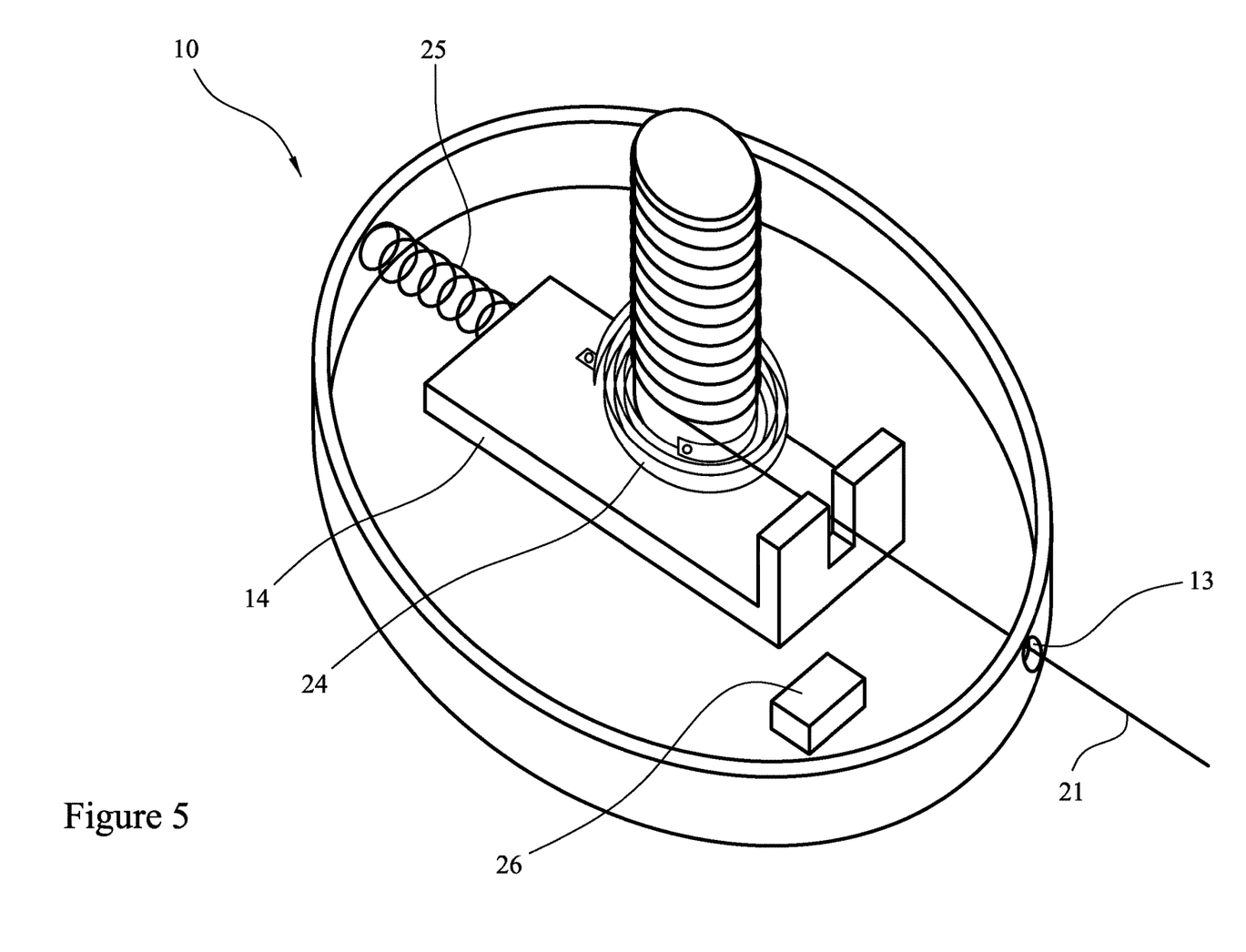
FIG. 5 shows a further embodiment of a device according to the invention.

Shown in FIG. 5 is an alternative embodiment of a orthostatic hypotension alleviation device 10 according to the invention. In this embodiment the carriage biasing spring 25 is on the opposite side of the carriage 14 to the aperture 13. In this embodiment the carriage biasing spring 25 is extended rather than compressed by the user in operation. Again, the spring constant of the carriage biasing spring 25 and the torque provided by the clockwork spring 24 are chosen such that when the tether 21 reaches the extended configuration from the retracted configuration the carriage biasing spring 25 is only partially extended. In this embodiment an end stop 26 is employed to prevent the carriage biasing spring 25 from extending beyond full extension and becoming plastically deformed.

In the embodiment of FIG. 2 when the tether 21 is in the retracted configuration and there is no tension in the tether 21, the carriage biasing spring 25 is in a neutral position i.e. neither extended nor compressed. In an alternative embodiment of the invention, when the device 10 is in this state the carriage biasing spring 25 is partially compressed so urging the carriage 14 as far from the aperture 13 as possible. The operation of this embodiment is the same as that of FIG. 2 except when the tether 21 is pulled the carriage 14 does not move towards the aperture 13 until the tether 21 reaches the extended configuration and the pulling force has been increased to a value which exceeds the force applied by the carriage biasing spring 25 on the carriage 14.

Figure 6:
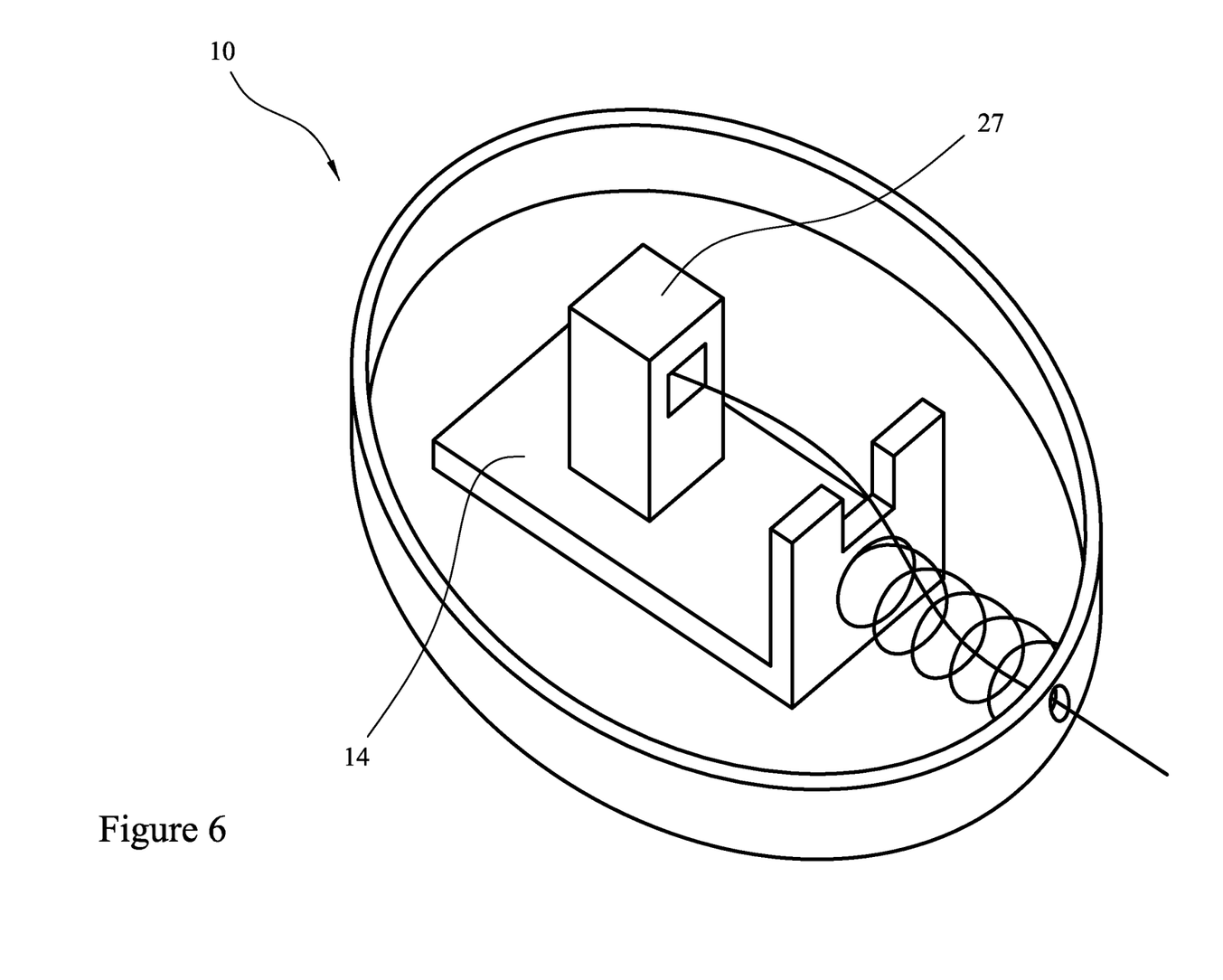
FIG. 6 shows a further embodiment of a device according to the invention.

Shown in FIG. 6 is a further embodiment of a device 10 according to the invention. In this embodiment the carriage 14 further comprises an inner casing 27 connected to the carriage plate 15. The spindle 19 and spindle biasing mechanism 24 are arranged within the inner casing 27. The spindle biasing mechanism 24 extends between the spindle 19 and inner casing 27. Preferably the inner casing 27 is detachably connected to the carriage plate 15 so that the inner casing 27, spindle 19, tether 21 and spindle biasing mechanism 24 can be removed and replaced as a single unit if required.

Figure 7A:
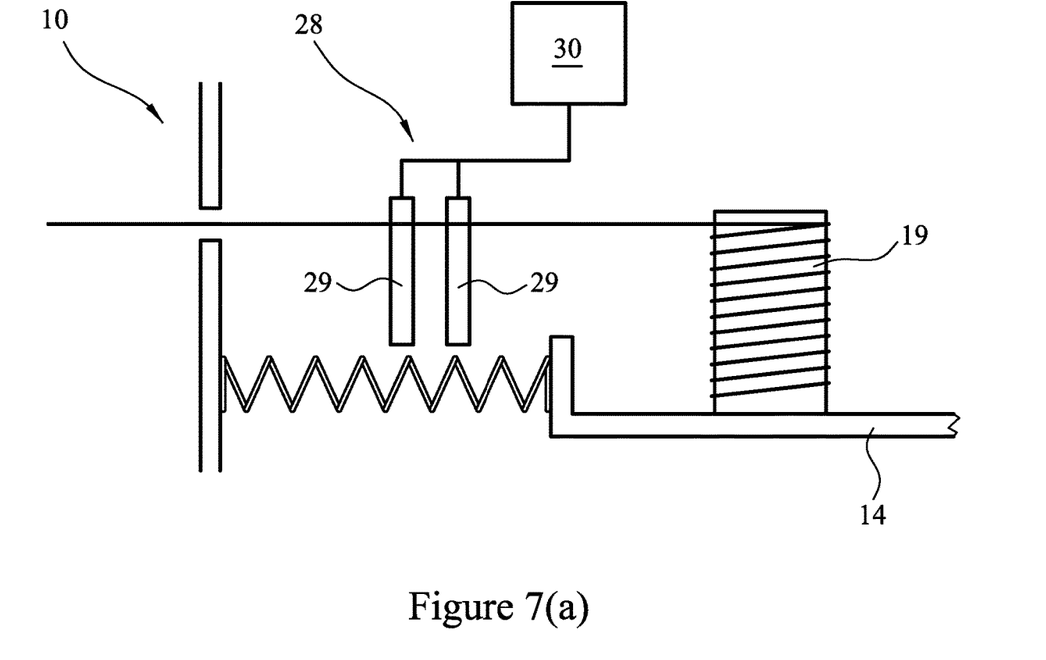
FIGS. 7(a) and 7(b) show a further embodiment of a device according to the invention.

As explained with reference to FIGS. 4(a) to 4(d), once the tether 21 reaches the extended configuration, the patient increases the pulling force so causing compression of the carriage biasing spring 25 and causing the carriage 14 to move towards the aperture 13. The position of the carriage 14 is therefore a function of the pulling force (or in other words, the tension in the tether 21). It is often desired that the patient only exerts a predetermined pulling force and in particular does not exceed the predetermined pulling force as this may have unwanted side effects, either on the patient or on the device 10. Shown in FIG. 7(a) in schematic form in vertical cross section is a further embodiment of a device 10 according to the invention. This embodiment further comprises a position detection mechanism 28 to determine the position of the carriage 14. The position detection mechanism 28 comprises first and second electrical contacts 29 arranged within the outer casing 11 with the first contact spaced 29 apart from but proximate to the second contact 29 as shown.

Figure 7B:
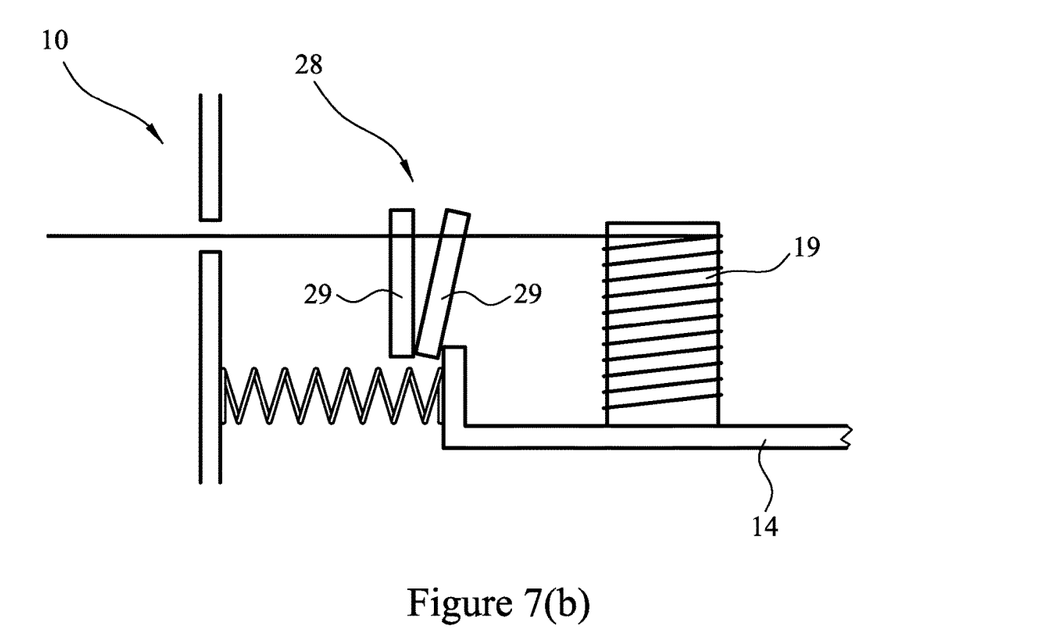

When the patient increases the pulling force on the tether 21 the carriage 14 moves towards and then abuts the first electrical contact 29. As the patient increases the pulling force further the carriage 14 moves closer to the aperture 13 bending the first electrical contact 29 towards the second electrical contact 29. As the pulling force applied by the patient reaches the predetermined pulling force the first electrical contact 29 abuts the second 29 as shown in FIG. 7(b). The device is designed such that at this point the tension in the tether 21 is typically in the range 20-100 N. An electrical circuit 30 is connected to the first and second electrical contacts 29 and is configured to produce an alert such as a sound or light when the two contacts 29 touch. The patient can simply pull the tether 21 with increasing force until the alert is raised and then hold the tether 21 in that position so performing the desired isometric exercise.

The electrical circuit 30 may provide additional functionality. The circuit 30 may include a timer which may produce a second alert once the patient has performed the isometric exercise for the desired amount of time. The timer may be programmable. The circuit 30 may further store data such as the time the exercise was performed and the duration of the exercise which can be downloaded for later analysis.

In a further embodiment of the invention the device 10 further comprises a blood pressure monitor and a pulse rate monitor. The blood pressure monitor is adapted to raise an alert if the patient's blood pressure exceeds a safe level during exercise. Similarly, the pulse rate monitor is adapted to raise an alert if the pulse rate of the patient exceeds a safe level during exercise. Both monitors may be configured to store data for later analysis. The device 10 may further comprise an accelerometer to measure movement of the device 10 whilst in use.

The invention claimed is:

1. The orthostatic hypotension alleviation device comprising an outer casing comprising an aperture extending therethrough;

a carriage arranged within the outer casing and configured to be reciprocally displaced towards and away from the aperture along a carriage displacement axis;

a spindle arranged on the carriage and configured to rotate about a spindle axis;

a tether at least partially wound around the spindle, the tether comprising a distal end extending through the aperture, the tether being arranged such that it can be extended from a retracted configuration to an extended configuration in which the tether is fully extended by pulling the distal end away from the aperture so rotating the spindle about the spindle axis;

a spindle biasing mechanism connected to the spindle and configured to apply a biasing torque to the spindle about the spindle axis so as to bias the tether towards the retracted configuration; and, a carriage biasing mechanism arranged within the outer casing connected to the carriage and configured to bias the carriage away from the aperture.

2. The orthostatic hypotension alleviation device as claimed in claim 1, wherein the carriage biasing mechanism is connected between the carriage and outer casing.

3. The orthostatic hypotension alleviation device as claimed in claim 2, wherein the carriage biasing mechanism comprises at least one carriage biasing spring extending along an axis substantially parallel to the carriage displacement axis.

4. The orthostatic hypotension alleviation device as claimed in claim 3, wherein the carriage biasing spring has a spring constant k, k having a value such that as the pulling force on the tether is increased to a value at which the spindle first begins to turn then at that value the carriage biasing spring is partially compressed or partially extended.

5. The orthostatic hypotension alleviation device as claimed in claim 3, wherein the carriage biasing spring has a spring constant k, the value of k being such that when a pulling force $P_c$ is applied to the tether which produces a torque on the spindle which balances the torque applied to the spindle by the spindle biasing mechanism, the carriage biasing spring is partially compressed or partially extended.

6. The orthostatic hypotension alleviation device as claimed in claim 1, wherein the spindle biasing mechanism is connected between the spindle and carriage.

7. The orthostatic hypotension alleviation device as claimed in claim 1, wherein the spindle biasing mechanism comprises a clockwork spring.

8. The orthostatic hypotension alleviation device as claimed in claim 1, wherein the carriage comprises a carriage plate and an inner casing connected to the carriage plate, the spindle and spindle biasing mechanism being arranged within the inner casing.

9. The orthostatic hypotension alleviation device as claimed in claim 8, wherein the inner casing is detachably connected to the carriage plate.

10. The orthostatic hypotension alleviation device as claimed in claim 1, further comprising a position detection mechanism for detecting the position of the carriage along the carriage displacement axis.

11. The orthostatic hypotension alleviation device as claimed in claim 10 wherein the position detection mechanism comprises first and second electrical contacts arranged inside the outer casing with the first contact proximate to the second, the first and second contact being arranged such that as the carriage moves along the displacement axis it abuts the first contact urging it into contact with the second contact.

12. The orthostatic hypotension alleviation device as claimed in claim 1, further comprising at least one of an accelerometer, a blood pressure sensor and a pulse monitor.

13. The orthostatic hypotension alleviation device as claimed in claim 1, further comprising a strap connected to the outer casing for connection to the human body.

14. The orthostatic hypotension alleviation device as claimed in claim 13, wherein the strap is a wrist strap.

* * * * *